United States Patent
Oguri et al.

(10) Patent No.: US 8,686,065 B2
(45) Date of Patent: Apr. 1, 2014

(54) ADHESIVE AGENT FOR ADHESION BETWEEN ALGINATE IMPRESSION MATERIAL AND IMPRESSION TRAY FOR DENTAL APPLICATIONS, AND KIT COMPRISING THE ADHESIVE AGENT

(75) Inventors: Makoto Oguri, Tokyo (JP); Hideki Kazama, Tokyo (JP)

(73) Assignee: Tokuyama Dental Corporation (JP)

( * ) Notice: Subject to any disclaimer, the term of this patent is extended or adjusted under 35 U.S.C. 154(b) by 539 days.

(21) Appl. No.: 12/529,135

(22) PCT Filed: Feb. 27, 2008

(86) PCT No.: PCT/JP2008/053393
§ 371 (c)(1),
(2), (4) Date: Jan. 19, 2010

(87) PCT Pub. No.: WO2008/105452
PCT Pub. Date: Sep. 4, 2008

(65) Prior Publication Data
US 2010/0120941 A1 May 13, 2010

(30) Foreign Application Priority Data

Feb. 28, 2007 (JP) .................................. 2007-048782
Jun. 29, 2007 (JP) .................................. 2007-171692
Nov. 14, 2007 (JP) .................................. 2007-295356

(51) Int. Cl.
*A61K 6/08* (2006.01)
*A61K 6/10* (2006.01)
*A61C 9/00* (2006.01)
*C08K 5/55* (2006.01)

(52) U.S. Cl.
USPC ............. 523/118; 523/109; 106/35; 433/214

(58) Field of Classification Search
USPC ....................... 523/109, 118; 106/35; 524/184
See application file for complete search history.

(56) References Cited

U.S. PATENT DOCUMENTS

| 3,564,091 | A | * | 2/1971 | Degray et al. .................... 514/64 |
| 3,575,891 | A | * | 4/1971 | Le Blanc et al. .............. 521/152 |
| 3,634,372 | A |   | 1/1972 | McFadden |
| 4,604,230 | A | * | 8/1986 | Goswami et al. .............. 252/514 |
| 4,726,986 | A | * | 2/1988 | Cannady et al. .............. 442/126 |
| 5,616,796 | A |   | 4/1997 | Pocius et al. |
| 7,041,714 | B2 | * | 5/2006 | Takeshita et al. ............. 523/118 |
| 2003/0100465 | A1 | * | 5/2003 | Kilkenny et al. ............. 510/384 |
| 2005/0196440 | A1 | * | 9/2005 | Masters et al. ................ 424/464 |
| 2005/0228113 | A1 | * | 10/2005 | Baumer et al. ................ 524/500 |
| 2005/0256223 | A1 | * | 11/2005 | Kolb et al. .................... 523/116 |

FOREIGN PATENT DOCUMENTS

| EP | 0336744 A2 | 10/1989 |
| JP | 402167384 A * | 6/1990 |
| JP | 9-278803 A | 10/1997 |
| JP | 10-175812 A | 6/1998 |
| JP | 2000-160106 A | 6/2000 |
| JP | 2001-17449 A | 1/2001 |
| JP | 2001081237 * | 3/2001 |
| JP | 2007-262010 A | 10/2007 |
| WO | 94/13235 A1 | 6/1994 |
| WO | 2004/071329 A1 | 8/2004 |

OTHER PUBLICATIONS

Supplementary European Search Report for Application No. EP 08 72 0941, date of completion of search, May 20, 2011.
Fujita, Akishi: "Water swellable medical polymer gel forming ionic group upon stimulation and manufacture of the gel", Database Caplus (Online) Chemical Abstract Service, Columbus, Ohio, US, Sep. 13, 1999 (abstract only).
Miyazaki Shozo et al.: "Chitosan and sodium alginate based bioadhesive tablets for intraoral drug delivery", Database Biosis (Online) Biosciences Information Service, Philadelphia, PA, US, 1994 (Abstract only).
International Search Report for PCT/JP2008/053393 mailed Apr. 8, 2008 with English translation.

* cited by examiner

*Primary Examiner* — Tae H Yoon
(74) *Attorney, Agent, or Firm* — Cantor Colburn LLP

(57) ABSTRACT

To improve an adhesive force of an adhesive agent between an impression material and a tray, and to stabilize the adhesive force therebetween, provided is an adhesive agent for the adhesion between an alginate impression material and an impression tray for dental applications, which includes a polyamine compound having two or more amino groups in a molecule and a solvent.

5 Claims, 1 Drawing Sheet

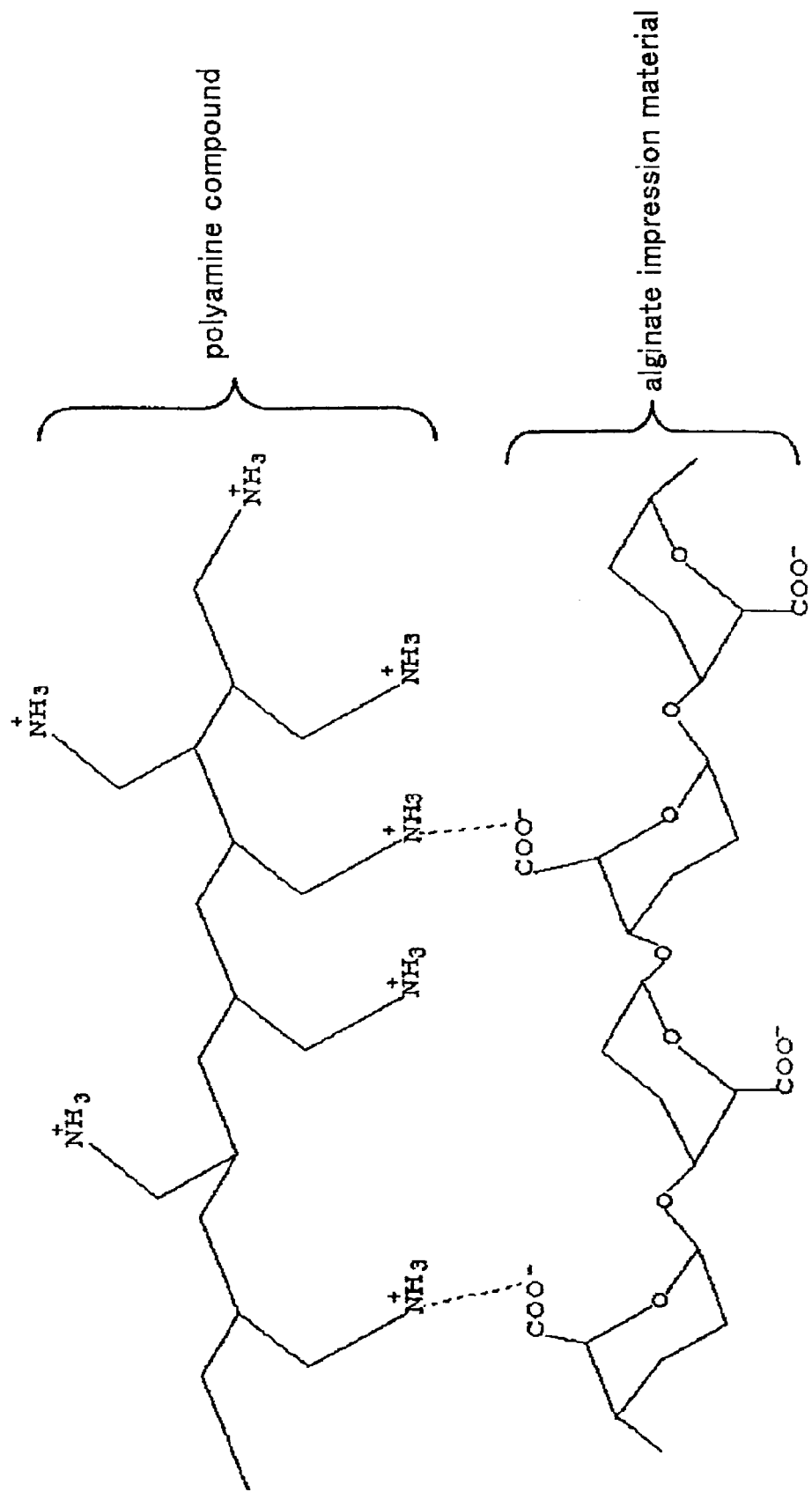

ADHESIVE AGENT FOR ADHESION BETWEEN ALGINATE IMPRESSION MATERIAL AND IMPRESSION TRAY FOR DENTAL APPLICATIONS, AND KIT COMPRISING THE ADHESIVE AGENT

This is a U.S. national stage of application No. PCT/JP2008/053393, filed on 27 Feb. 2008. Priority under 35 U.S.C. §119(a) and 35 U.S.C. §365(b) is claimed from Japanese Application Nos. JP 2007-048782, filed 28 Feb. 2007, JP 2007-171692, filed 29 Jun. 2007, and JP 2007-295356, filed 14 Nov. 2007, the disclosures of each of which are also incorporated herein by reference.

TECHNICAL FIELD

The present invention relates to an adhesive agent for adhesion between an alginate impression material and an impression tray for dental applications, and a kit including the adhesive agent.

BACKGROUND ART

In the case where a treatment for restoring cast crown or a treatment for defect prosthesis is required to restore a tooth, first, a cast of an abutment tooth is taken. Next, the taken cast is used to prepare a model made of plaster. Then, a material which substitutes for a damaged portion of the tooth is produced based on the model, and the resultant material is attached to the abutment tooth. The cast of the abutment tooth is referred to as impression, and a cured product to be used for taking the impression is referred to as impression material.

In general, an alginate impression material, agar impression material, silicone gum impression material, polysulfide gum impression material, or polyether gum impression material is used as an impression material. Of those, the alginate impression material is inexpensive and easy to handle, and hence the material is most widely used. The alginate impression material includes a base material containing mainly an alginate and a curing material containing mainly calcium sulfate. When the base material and curing material are kneaded in the presence of water, a gel-like cured product is obtained.

A process for taking an impression using an alginate impression material is performed according to the following procedures. First, a product prepared by kneading a base material and a curing material before curing is placed on an impression tray which is made to be similar shape of arrangement of teeth. Next, the tray where the impression material is placed is pressed against the teeth so that the tray covers the teeth in the oral cavity. Then, after the impression material is cured, an integrated product of the impression material and tray is removed from the teeth and taken out from the oral cavity.

Trays to be used for taking impressions are broadly divided into two types: ready-made trays and custom-made trays. The ready-made trays are ones which have predetermined sizes and shapes. Specific examples of the ready-made trays include metallic trays such as stainless, brass, and chrome-plated brass trays. Meanwhile, the custom-made trays are ones which have shapes suitable for individuals. Specific examples of the custom-made trays include resin trays which include a polymethacrylate and modeling compound trays which include a thermoplastic resin.

The alginate impression material has low adhesion property to the above-mentioned trays. Therefore, when the impression material is removed from teeth, the material may peel off from the tray. Peeling of the impression material from the tray may cause a significant change in the shape of the impression, so there occurs a problem that an impression with high accuracy cannot be obtained.

To solve the above-mentioned problems, net-like trays, undercut-like trays, or trays having punch holes may be used. When a tray having one of those shapes is used, the holding force between the impression material and tray is improved because the area of the impression material which contacts with the tray increases. Therefore, it is possible to prevent the impression material from peeling off from the tray.

On the other hand, in the case of using trays other than trays having the above-mentioned shapes, i.e., in the case of using, for example, ready-made or custom-made trays having plate-like shapes, it is necessary to enhance the holding force between the impression material and tray by another method. As one of the methods, a method for adhesion of a tray to an impression material using an adhesive agent containing an alkaline metal earth has been suggested (see Patent Document 1, for example).

Patent Document 1: JP 10-175812 A

SUMMARY OF THE INVENTION

However, the above-mentioned conventional techniques have the following problems. If a tray is produced so as to have a specific shape such as a net-like shape, the cost of the tray increases. Meanwhile, it is required to further enhance the adhesive force compared with the case where the adhesive agent containing an alkaline earth metal compound is used.

Meanwhile, after production of a resin tray, in order to remove organic substances and improve adhesiveness on the surface, the tray is subjected to a treatment to make roughness on the tray surface with a sandblast or a grinding bar. However, on a surface where such a treatment is not completely performed, the adhesive force varies depending on the smoothness degree on the tray surface. Therefore, it is desired to stabilize the adhesive force of the adhesive agent between the impression material and tray regardless of the surface roughness degree on the tray surface.

Accordingly, at least an embodiment of the invention further improves the adhesive force of an adhesive agent between an impression material and a tray and to stabilize the adhesive force.

In order to accomplish the above, the inventors of the present invention have conducted keen study. As a result, the inventors of the present invention have found that, when a composition obtained by mixing a polyamine compound having two or more amino groups in a molecule in water or an organic solvent is placed between a tray and an alginate impression material, a stable and high adhesive force is achieved between the tray and alginate impression material, and have completed the present invention.

That is, the present invention provides an adhesive agent for adhesion between an alginate impression material and an impression tray for dental applications, comprising (A) a polyamine compound having two or more amino groups in a molecule and (B) a solvent.

Further, another aspect of the present invention provides an adhesive agent for adhesion between an alginate impression material and an impression tray for dental applications, further comprising at least one of (C) an aryl borate compound and (D) an organic peroxide.

If an adhesive agent having the above composition is employed, for example, an adhesive agent containing (C) the aryl borate compound can improve stability of adhesiveness between an alginate impression material and an impression tray. Meanwhile, an adhesive agent containing (D) the organic peroxide can strengthen the adhesive force between an alginate impression material and an impression tray. Moreover, an adhesive agent containing both (C) the aryl borate and (D) the organic peroxide can effectively prevent the alginate impression material from peeling off from the impression tray without being affected by the roughness on the tray surface.

Further, in another aspect of the present invention, in the case where the adhesive agent contains (C) the aryl borate compound, (C) the aryl borate compound is a compound represented by a general formula (1):

[Chem 1]

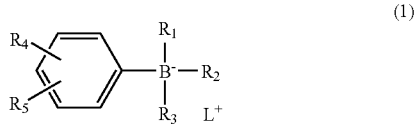

(1)

where: $R_1$, $R_2$, and $R_3$ each independently represent an alkyl group, an aryl group, or an alkenyl group; $R_4$ and $R_5$ each independently represent a hydrogen atom, a halogen atom, a nitro group, an alkyl group, an alkoxy group, or a phenyl group; and $L^+$ represents a metallic cation, a tertiary or quaternary ammonium ion, a quaternary pyridinium ion, a quaternary quinolinium ion, or a quaternary phosphonium ion.

If an adhesive agent having the above composition is employed, it is possible to improve stability of adhesiveness more between the alginate impression material and impression tray. Therefore, the adhesive agent can effectively prevent the alginate impression material from peeling off from the impression tray without being affected by the roughness on the tray surface.

Further, in another aspect of the present invention, an adhesive agent for adhesion between an alginate impression material and an impression tray for dental applications comprising (A) a polyamine compound having two or more amino groups in a molecule, (B) a solvent, and (D) an organic peroxide further comprises, together with (D) the organic peroxide, (E) a compound represented by the following general formula (2), where $R^6$ and $R^7$ each independently represent a hydrogen atom or an alkyl group with 1 to 3 carbon atoms.

[Chem 2]

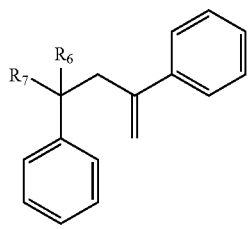

(2)

If an adhesive agent having the above composition is employed, it is possible to improve preservation stability of the adhesive agent for adhesion between an alginate impression material and an impression tray for dental applications, which contains an organic peroxide.

Further, another aspect of the present invention provides an adhesive agent for adhesion between an alginate impression material and an impression tray for dental applications, wherein (B) the solvent is at least one selected from alcohols, acetone, and acetate esters.

If an adhesive agent having the above composition is employed, it is possible to prepare an adhesive agent for adhesion between an alginate impression material and an impression tray for dental applications, which is easily subjected to a drying step as described below, is highly permeable to a resin tray and a modeling compound tray, and has low toxicity.

Further, another aspect of the present invention provides an adhesive agent for adhesion between an alginate impression material and an impression tray for dental applications, wherein a polyamine compound having 5 or more amino groups in a molecule is used as the polyamine compound.

If the adhesive agent for adhesion between an alginate impression material and an impression tray for dental applications is employed, it is possible to further enhance the adhesive force between not only a metallic tray but also a resin tray or a modeling compound tray and an alginate impression material.

Further, another aspect of the present invention provides a kit comprising the adhesive agent for adhesion between an alginate impression material and an impression tray for dental applications and a paste-type alginate impression material.

If the kit is employed, it is not necessary to prepare the adhesive agent and alginate impression material individually, which is convenient. Even if a kit including a paste-type alginate impression material which is easy to handle is employed, the impression material is difficult to peel off from the tray when the impression material is removed from the teeth.

According to the present invention, it is possible to further improve the adhesive force of an adhesive agent between an impression material and a tray and to stabilize the adhesive force.

BRIEF DESCRIPTION OF THE DRAWING

FIG. 1 is a schematic view illustrating a cross-linking between an alginate impression material and a polyamine compound contained in an adhesive agent.

BEST MODE FOR CARRYING OUT THE INVENTION

Preferred embodiments of the adhesive agent for adhesion between an alginate impression material and an impression tray for dental applications according to the present invention is hereinafter described. However, the present invention is not limited by the following embodiments.

FIG. 1 is a schematic view illustrating cross-linkage between an alginate impression material and a polyamine compound in an adhesive agent.

When a polyamine compound having two or more amino groups (—$NH_2$) in a molecule is used as an adhesive agent, cross-linkings are formed between the amino groups in the polyamine compound and the carboxyl groups in the alginate impression material as shown in FIG. 1. Further, the polyamine compound has high affinity for the tray material, and therefore, when the compound is brought into contact with the tray material, the compound is attached firmly to the material. Accordingly, the tray can be adhered to the alginate impression material stably and firmly via the polyamine compound.

(A) Polyamine Compound Containing Two or More Amino Groups in a Molecule

Specifically, as the polyamine compound used in an adhesive agent according to the embodiments of the present invention, there are suitably used: an aliphatic polyamine compound having two or more amino groups in a molecule such as ethylene diamine, 1,4-butanediamine, 1,7-heptanediamine, 4-(aminomethyl)-1,8-octanediamine, or tris(2-aminoethyl)amine; an alicyclic polyamine compound having two or more amino groups in a molecule such as 1,2-diaminocyclohexane, 1,4-diaminocyclohexane, or 1,3-cyclohexane bis (methylamine); an aromatic polyamine compound having two or more amino groups in a molecule such as 1,3-phenylene diamine, 3,3'-methylenedianiline, 1,2,4-triaminobenzene, diaminoalkanes, 1,3,5-triazine-2,4,6-triamine, or 3,3'-diaminobenzidine; and a polymer or a copolymer formed of a monomer having one or more amino groups such as such as polyallylamine, polyethyleneamine, polyvinylamine, polyethyleneimine, polyornithine, polylysine, or chitosan. Those compounds may be used alone or two or more of them may be used in mixture.

Though there is no particular limitation on the molecular weight of the polyamine compound to be used in the adhesive agent according to the embodiment of the present invention, the molecular weight is preferably 500,000 or less from the standpoint of solubility in a solvent. Moreover, the molecular weight is more preferably 1,000 to 20,000. Meanwhile, in the case where a polyamine compound having a molecular weight of 2,000 or more is used, in order to achieve a sufficiently high adhesive force, the polyamine compound preferably has one or more amino groups for each 300 of the molecular weight, more preferably one or more amino groups for each 200 of the molecular weight. In addition, 100 parts by mass of the adhesive agent according to the embodiment of the present invention preferably contains the polyamine compound in an amount ranging from 1 part by mass to 50 parts by mass. Moreover, 100 parts by mass of the adhesive agent contains the polyamine compound in an amount ranging from, particularly preferably, 3 parts by mass to 40 parts by mass, most preferably 10 parts by mass to 35 parts by mass.

The adhesive agent according to the embodiment of the present invention can preferably be used for, at least, adhesion between a metallic tray and an alginate impression material. If an adhesive agent containing a polyamine compound having 5 or more, more preferably 15 or more amino groups in a molecule, such as polyallylamine, polyethyleneamine, polyvinylamine, polyethyleneimine, polyornithine, polylysine, or chitosan, is used, it is possible to achieve stable adhesion between a resin tray or a modeling compound tray and an alginate impression material. Examples of the metallic tray suitable for the adhesive agent according to the embodiment of the present invention include known trays such as brass trays, chromed brass trays, and stainless trays. In addition, examples of the resin tray include a tray obtained by mixing and polymerizing a methacrylate polymer powder and methyl methacrylate, a thermoplastic tray which contains mainly a natural resin, and a ready-made tray which is made of polystyrene and is cut before use. Meanwhile, examples of the modeling compound tray include a tray containing mainly a natural thermoplastic resin such as corpearl and a synthetic thermoplastic resin such as a phthalate resin.

(B) Solvent

The solvent to be used in the adhesive agent according to the embodiment of the present invention is used for improving the operability of the adhesive agent. Therefore, any known solvent excellent in fluidity and affinity for a tray can be used without any limitation. Specific examples thereof include: water; an alcohol such as methanol, ethanol, isopropyl alcohol, or butanol; a ketone such as acetone or methyl ethyl ketone; an aromatic hydrocarbon such as toluene, xylene, or benzene; a chlorinated solvent such as methylene chloride or chloroform; and an aliphatic hydrocarbon such as hexane, pentane, or butane. In particular, a solvent having high volatility and low toxicity, such as ethanol or isopropyl alcohol, is suitably used because a drying step as described below can be easily performed. Moreover, an alcohol such as ethanol or isopropyl alcohol; acetone; and an acetate ester such as ethyl acetate or butyl acetate are particularly suitably used because those solvents have high ability to penetrate a resin tray and a modeling compound tray and have low toxicity.

(C) Aryl Borate Compound

Any known compound having at least one boron-aryl bond in the molecule can be used as the aryl borate compound to be used in the adhesive agent according to the embodiment of the present invention without any limitation. If such an aryl borate compound is used together with the polyamine compound, it is possible to achieve stable adhesive force particularly to a resin tray and a modeling compound tray. In particular, even on a tray surface where a treatment to make roughness on the tray surface is not performed with a sandblast or grinding bar, it is possible to further stabilize the adhesive force of the adhesive agent between an impression material and a tray. Moreover, the compound does not require careful handling at the time of manufacture, like an organic peroxide. On the other hand, a borate compound having no boron-aryl bond has very poor stability and is decomposed upon easily reacting with oxygen in the air, which makes it impractical to use the compound.

From the viewpoint of preservation stability, the aryl borate compound to be used in the present invention is preferably a compound represented by the following general formula (1):

[Chem 1]

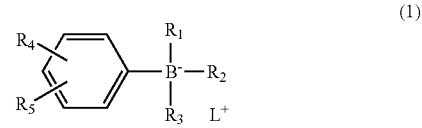

(1)

where: $R_1$, $R_2$, and $R_3$ each independently represent an alkyl group, an aryl group, or an alkenyl group; $R_4$ and $R_5$ each independently represent a hydrogen atom, a halogen atom, a nitro group, an alkyl group, an alkoxy group, or a phenyl group; and represents a metallic cation, a tertiary or quaternary ammonium ion, a quaternary pyridinium ion, a quaternary quinolinium ion, or a quaternary phosphonium ion.

In the above general formula (1), $R_1$, $R_2$, and $R_3$ each independently represent an alkyl group, an aryl group, or an alkenyl group. In addition, the groups may have a substituent.

There is no particular limitation on the alkyl group, and the alkyl group may be linear or branched. The alkyl group is preferably an alkyl group with 3 to 30 carbon atoms, more preferably a linear alkyl group with 4 to 20 carbon atoms. Specific examples thereof include an n-butyl group, an n-octyl group, an n-dodecyl group, and an n-hexadecyl group. Meanwhile, examples of the substituent in the alkyl group include: a halogen atom such as a fluorine atom, a chlorine atom, and a bromine atom; a hydroxyl group; a nitro group; a cyano group; an aryl group with 6 to 10 carbon atoms such as a phenyl group, a nitrophenyl group, and a chlorophenyl group; an alkoxy group with 1 to 5 carbon atoms such as a methoxy group, an ethoxy group, and a propyl group; and an acyl group with 2 to 5 carbon atoms such as an acetyl group. There is no particular limitation on the number and position of the substituent.

Also, there is no particular limitation on the aryl group, and the aryl group may be a known one. The aryl group is preferably a substituted or unsubstituted aryl group fused with single ring or two or three rings. Examples of the substituent include: those exemplified as the substituents of the alkyl group; and an alkyl group with 1 to 5 carbon atoms such as a methyl group, an ethyl group, and a butyl group.

Specific examples of the substituted or unsubstituted aryl group include a phenyl group, a 1- or 2-naphthyl group, a 1-, 2-, or 9-anthryl group, a 1-, 2-, 3-, 4-, or 9-phenanthryl group, a p-fluorophenyl group, a p-chlorophenyl group, a (3,5-bis-trifluoromethyl)phenyl group, a 3,5-bis(1,1,1,3,3,3-hexafluoro-2-methoxy-2-propyl) phenyl group, a p-nitrophenyl group, a m-nitrophenyl group, a p-butylphenyl group, a m-butylphenyl group, a p-butyloxyphenyl group, a m-butyloxyphenyl group, a p-octyloxyphenyl group, a m-octyloxyphenyl group.

Though there is no particular limitation on the alkenyl group, the alkenyl group is preferably an alkenyl group with 4 to 20 carbon atoms. Examples of a substituent of the alkenyl group include those exemplified as the substituent of the alkyl group.

In the above general formula (1), $R_4$ and $R_5$ each independently represent a hydrogen atom, a halogen atom, a nitro group, an alkyl group, an alkoxy group, or a phenyl group. Of those, the alkyl group, the alkoxy group, and the phenyl group are an alkyl group or an alkoxy group which may have a substituent, or ones which may have a substituent.

There is no particular limitation on the alkyl group or the alkoxy group, and the groups may be linear or branched. The alkyl group or the alkoxy group are preferably an alkyl group or an alkoxy group with 1 to 10 carbon atoms. Meanwhile, examples of substituents of the alkyl group or the alkoxy group include those exemplified as substituents of the alkyl groups represented by $R_1$ to $R_3$ described above. Specific examples of the alkyl group which may have the substituent include a methyl group, an ethyl group, an n- or i-propyl group, an n-, or t-butyl group, a chloromethyl group, a trifluoromethyl group, a methoxymethyl group, and a 1,1,1,3,3,3-hexafluoro-2-methoxy-2-propyl group. Specific examples of the alkoxy group which may have a substituent include a methoxy group, an ethoxy group, a 1- or 2-propoxy group, a 1- or 2-butoxy group, a 1-, 2-, or 3-octyloxy group, and a chloromethoxy group.

In addition, there is no particular limitation on the substituent in the phenyl group, and specific examples thereof include those exemplified as substituents of the aryl groups represented by $R_1$ to $R_3$. described above In the above general formula (1), represents a metallic cation, a tertiary or quaternary ammonium ion, a quaternary pyridinium ion, a quaternary quinolinium ion, or a quaternary phosphonium ion.

Preferable examples of the metal cation include an alkali metal cation such as sodium ion, lithium ion, or potassium ion; and an alkaline earth metal cation such as magnesium ion. The tertiary or quaternary ammonium ion is exemplified by tetrabutyl ammonium ion, tetramethyl ammonium ion, tetraethyl ammonium ion, tributyl ammonium ion, and triethanol ammonium ion. The quaternary pyridinium ion is exemplified by methylquinclinium ion, ethyl quinolinium ion, and butyl quinolinium ion. The quaternary phosphonium ion is exemplified by tetrabutylphosphonium ion and methyltriphenylphosphonium ion.

Specific examples of the aryl borate compound represented by the above formula (1) include borate compounds having one boron-aryl bond in a molecule such as a sodium salt, lithium salt, potassium salt, magnesium salt, tetrabutylammonium salt, tetramethylammonium salt, tetraethylammonium salt, tributylamine salt, triethanolamine salt, methylpyridinium salt, ethylpyridinium salt, butylpyridinium salt, methylquinolinium salt, ethylquinolinium salt, and butylquinolinium salt of trialkylphenylboron, trialkyl(p-chlorophenyl)boron, trialkyl(p-fluorophenyl)boron, trialkyl(3,5-bistrifluoromethyl)phenylboron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron, and trialkyl(m-octyloxyphenyl)boron (with the provision that in each of the compounds, alkyl represents one of n-butyl, n-octyl, and n-dodecyl).

As the borate compounds having two boron-aryl bonds in a molecule, there can be exemplified a sodium salt, lithium salt, potassium salt, magnesium salt, tetrabutylammonium salt, tetramethylammonium salt, tetraethylammonium salt, tributylamine salt, triethanolamine salt, methylpyridinium salt, ethylpyridinium salt, butylpyridinium salt, methylquinolinium salt, ethylquinolinium salt, butylquinolinium salt, or the like of dialkyldiphenylboron, dialkyldi(p-chlorophenyl)boron, dialkyldi(p-fluorophenyl)boron, dialkyldi(3,5-bistrifluoromethyl)phenylboron, dialkyldi[3,5-bis(1,1,1,3,3,3-hexafluoro-2-methoxy-2-propyl)phenyl]boron, dialkyl(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi(p-octyloxyphenyl)boron, and dialkyldi(m-octyloxyphenyl)boron (with the provision that in each of the compounds, alkyl represents one of n-butyl, n-octyl, and n-dodecyl).

Further, as the borate compounds having three boron-aryl bonds in a molecule, there can be exemplified a sodium salt, lithium salt, potassium salt, magnesium salt, tetrabutylammonium salt, tetramethylammonium salt, tetraethylammonium salt, tributylamine salt, triethanolamine salt, methylpyridinium salt, ethylpyridinium salt, butylpyridinium salt, methylquinolinium salt, ethylquinolinium salt, butylquinolinium salt, or the like of monoalkyltriphenylboron, monoalkyltris(p-chlorophenyl)boron, monoalkyltris(p-fluorophenyl)boron, monoalkyltris(3,5-bistrifluoromethyl)phenylboron, monoalkyltris[3,5-bis(1,1,1,3,3,3-hexafluoro-2-methoxy-2-propy 1)phenyl]boron, monoalkyltris(p-nitrophenyl)boron, monoalkyltris(m-nitrophenyl)boron, monoalkyltris(p-butylphenyl)boron, monoalkyltris(m-butylphenyl)boron, monoalkyltris(p-butyloxyphenyl)boron, monoalkyltris(m-butyloxyphenyl)boron, monoalkyltris(p-octyloxyphenyl)boron, and monoalkyltris(m-octyloxyphenyl)boron (with the provision that in each of the compounds, alkyl represents one of n-butyl, n-octyl, and n-dodecyl).

As the borate compounds having four boron-aryl bonds in a molecule, there can be exemplified a sodium salt, lithium salt, potassium salt, magnesium salt, tetrabutylammonium salt, tetramethylammonium salt, tetraethylammonium salt, tributylamine salt, triethanolamine salt, methylpyridinium salt, ethylpyridinium salt, butylpyridinium salt, methylquinolinium salt, ethylquinolinium salt, butylquinolinium salt, or the like of tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, and tetrakis(m-octyloxyphenyl)boron (with the provision that in each of the compounds, alkyl represents one of n-butyl, n-octyl, and n-dodecyl).

Of those, it is preferable to use an aryl borate compound having three or four boron-aryl bonds in a molecule from the viewpoint of adhesion, and it is more preferable to use an aryl borate compound having four boron-aryl bonds from the viewpoint of ease of handling, synthesis, and availability. The aryl borate compound is particularly preferably an aryl borate compound wherein all of $R_1$, $R_2$, $R_3$, and a group represented by:

[Chem 3]

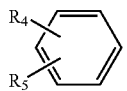

are the same group, that is, wherein the boron atoms are replaced by the same four aryl groups.

Meanwhile, $L^+$ is preferably a tertiary or quaternary ammonium ion, more preferably a tertiary ammonium ion.

Those aryl borate compounds may be used singly, or a mixture of two or more of the compounds may be used. In order to achieve a sufficiently stable adhesive force in the adhesive agent according to the embodiment of the present invention, 100 parts by mass of the adhesive agent contain the aryl borate compound in an amount ranging, preferably from 0.1 part by mass to 30 parts by mass, particularly preferably from 1 part by mass to 20 parts by mass.

(D) Organic Peroxide

In the adhesive agent according to the embodiment of the present invention, the organic peroxide can be used to further improve the adhesive ability of the adhesive agent. Examples of the organic peroxides include diacyl peroxides, peroxy esters, dialkyl peroxides, peroxy dicarbonates, peroxy ketals, ketone peroxides, and hydroperoxides. Of those, by using diacyl peroxides, an impression material is adhered to the tray material strongly. Specific examples of the diacyl peroxides include benzoyl peroxide, stearoyl peroxide, 2,4-dichlorobenzoyl peroxide, and m-toluoyl peroxide. In order to achieve a sufficiently strong adhesive force, 100 parts by mass of the adhesive agent contain the organic peroxide in an amount ranging, preferably from 0.1 part by mass to 30 parts by mass, particularly preferably from 1 part by mass to 12 parts by mass.

(E) Compound Represented by General Formula (2)

In the adhesive agent according to the embodiment of the present invention, a compound represented by the following general formula (2) (wherein $R_6$ and $R_7$ each independently represent a hydrogen atom or an alkyl group with 1 to 3 carbon atoms) (hereinafter, referred to as α-alkylstyrene dimer) is used to improve preservation stability of the adhesive agent containing the organic peroxide.

[Chem 2]

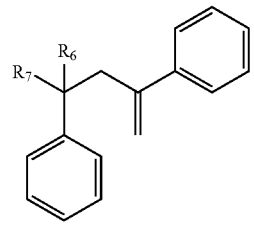

(2)

Specifically, if the α-alkylstyrene dimer is added to the adhesive agent, it is possible to effectively prevent a decrease in the adhesive force of the adhesive agent after long-term preservation compared with the initial adhesive force. Though there is no particular limitation on the α-alkylstyrene dimer represented by the above general formula (2), the dimer may be 2,4-diphenyl-4-methyl-1-pentene (both of $R_6$ and $R_7$ are methyl groups) or 2,4-diphenyl-4-ethyl-1-hexene (both of $R_6$ and $R_7$ are ethyl groups). In addition, the dimer may be an α-alkylstyrene dimer where $R_6$ and $R_7$ are different from each other, for example, 2,4-diphenyl-4-methyl-1-hexene ($R_6$ is a methyl group, and $R_7$ is an ethyl group). In order to sufficiently improve preservation stability of the adhesive agent, 100 parts by mass of the adhesive agent contain the α-alkylstyrene dimer in an amount ranging, preferably from 0.05 part by mass to 5 parts by mass, more preferably from 0.1 part by mass to 3 parts by mass.

There is no particular limitation on a method of using the adhesive agent according to the embodiment of the present invention. In general, a method involving applying the adhesive agent with a brush, spatula, ink brush, or roller on a tray or spraying the adhesive agent on a tray may be employed.

After applying or spraying the adhesive agent on the tray, drying is preferably performed to volatize an excess solvent. As a method of the drying, for example, natural drying, heat drying, air drying, reduced-pressure drying, or hot-air drying (combination of the heat drying and air drying) is preferably employed.

Any known alginate impression material can be used as the impression material where the adhesive agent according to the embodiment of the present invention is applied without any limitation. The adhesive agent can be used for both an alginate impression material which is preserved in a paste state (hereinafter, referred to as paste-type alginate impression material) and an alginate impression material which is used by mixing powder and water before use (hereinafter, referred to as powder-type alginate impression material). Examples of the paste-type alginate impression material include a product used by mixing a base material paste containing mainly an alginate and a curing material paste containing mainly calcium sulfate before use. Specific examples of the powder-type alginate impression material include a product used by mixing water in powder containing mainly an alginate and calcium sulfate before use.

In more detail, in the powder-type arginate impression material, the powder is formed of potassium arginate, a silica powder, zinc oxide, magnesium oxide, sodium triphosphate, fluorinated potassium titanate, calcium sulfate, or the like.

On the other hand, the base material paste used in the arginate impression material which is used by mixing a paste is formed of potassium arginate, a silica powder, potassium hydroxide, polyacrylic acid, water, or the like. Similarly, the curing material paste is formed of a particulate silica, liquid paraffin, zinc oxide, magnesium oxide, sodium triphosphate, fluorinated potassium titanate, superfine particulate silica, a surfactant, calcium sulfate, and the like. For example, in order to prevent the solvent from volatilizing and curing during preservation, such a paste-type alginate impression material contains a larger amount of liquid paraffin or a surfactant compared with the powder-type alginate impression material. For example, the paste-type alginate impression material contains 10 to 200 parts by mass of a poorly water-soluble liquid compound such as liquid paraffin and 0.1 to 10 parts by mass of a surfactant with respect to 100 parts by mass of calcium sulfate.

The paste-type alginate impression material contains a larger amount of liquid paraffin or the like, and hence, the material easily peels off from the tray surface. However, the adhesive agent according to the embodiment of the present invention has improved adhesive force between the paste-type alginate impression material and tray, thereby achieving a stable adhesive force. Therefore, if a kit including the adhesive agent according to the embodiment of the present invention and the paste-type alginate impression material is produced, the kit makes it possible to eliminate the need for weighing and mixing a powdery component and a liquid component before using the alginate impression material and to take an impression with uniform, smooth surface and high accuracy.

EXAMPLES

The present invention is hereinafter specifically described with reference to examples to which only, however, the invention is in no way limited.

ated based on a ratio of the area of the interface between the impression material and tray where cohesive failure was caused. In all adhesion tests, a paste-type alginate impression material "AP-1 Paste" (manufactured by Tokuyama Dental Corporation), which had been kneaded by AP mixer II (manufactured by Tokuyama Dental Corporation), was used.

(2) Type of Tray

X: A nickel-plated brass tray "COE104" (manufactured by GC Corporation) was used as a metallic tray.

Y: A tray obtained by forming "OSTRON II" (manufactured by GC Corporation) into a plate by curing was used as a resin tray.

Z: "Modeling Compound (neutral)" (manufactured by GC Corporation) was used as a modeling compound tray.

(3) Reference of Evaluation

⊚ (Double Circle): When the impression material is peeled off from the tray by hand, cohesive failure is caused at the entirety of the impression material.

○ (Single Circle): When the impression material is peeled off from the tray by hand, cohesive failure is caused at many parts of the impression material while a part of the material peels off from the interface between the material and tray.

Δ (Triangle): When the impression material is peeled off from the tray by hand, cohesive failure is caused at a part of the impression material while many parts of the material peel off from the interface between the material and tray.

x (cross): When the impression material is peeled off from the tray by hand, the entirety of the impression material easily peels off from the interface between the material and tray.

TABLE 1

|  | Polyamine compound (molecular weight)/parts by mass | Solvent/parts by mass | Organic peroxide/ parts by mass | Adhesiveness to tray (initial) | | |
| --- | --- | --- | --- | --- | --- | --- |
|  |  |  |  | X | Y | Z |
| Example 1 | Ethylenediamine/30 | Ethanol/70 | — | Δ | X | X |
| Example 2 | 1,7-heptanediamine/30 | Ethanol/70 | — | Δ | X | X |
| Example 3 | 3,3'-diaminobenzidine/10 | Acetone/90 | — | Δ | X | X |
| Example 4 | Chitosan (984)/20 | Ethanol/60 + distilled water/20 | — | ○ | Δ | Δ |
| Example 5 | Polyallylamine (1,000)/10 | Ethanol/50 + distilled water/40 | — | ⊚ | Δ | Δ |
| Example 6 | Polyallylamine (1,000)/30 | Ethanol/50 + distilled water/20 | — | ⊚ | Δ | ○ |
| Example 7 | Polyallylamine (3,000)/5 | Ethanol/95 | — | ○ | Δ | Δ |
| Example 8 | Polyallylamine (3,000)/10 | Ethanol/90 | — | ⊚ | Δ | Δ |
| Example 9 | Polyallylamine (3,000)/20 | Ethanol/80 | — | ⊚ | Δ | Δ |
| Example 10 | Polyallylamine (3,000)/30 | Ethanol/70 | — | ⊚ | Δ | ○ |
| Example 11 | Polyallylamine (15,000)/15 | Ethanol/85 | — | ⊚ | Δ | Δ |
| Example 12 | Polyallylamine (15,000)/15 | Isopropyl alcohol/85 | — | ⊚ | Δ | Δ |
| Example 13 | Polyallylamine (15,000)/15 | Acetone/85 | — | ⊚ | Δ | Δ |
| Example 14 | Polyallylamine (15,000)/15 | Distilled water/85 | — | ⊚ | Δ | Δ |
| Example 15 | Polylysine (3,500)/20 | Ethanol/40 + distilled water/40 | — | ⊚ | Δ | Δ |

First, an adhesion test was performed for adhesive agents each containing a polyamine compound and a solvent and not containing an organic peroxide and an aryl borate compound. Table 1 shows the evaluation results. The adhesion test method, types of trays used, and evaluation method are shown in the following items (1), (2), and (3), respectively.

(1) Adhesion Test Method

Adhesive agents prepared previously were applied onto the trays described in the item (2) by using an ink brush, and the excess solvent was volatized by air blow. Then, a kneaded alginate impression material was placed on the trays, and the trays were subject to weight bearing (300 g) and allowed to stand at 37° C. for 3 minutes. Thereafter, the cured impression materials were peeled off from the trays.

Subsequently, in accordance with the reference of evaluation described in the item (3), the adhesive ability was evalu- Examples 1 to 4

Adhesive agents of Examples 1 to 4 having the compositions shown in Table 1 were prepared using ethylenediamine and 1,7-heptanediamine as polyamine compounds having two amino groups in a molecule, using 3,3'-diaminobenzidine as a polyamine compound having four amino groups in a molecule, and using chitosan (molecular weight: 984) as a polyamine compound having six amino groups in a molecule.

Metallic trays where the adhesive agents of Examples 1 to 4 were applied were found to adhere firmly to the alginate impression material. Meanwhile, the adhesion of Example 4 prepared using chitosan having six amino groups in a molecule was found to have a relatively high adhesive force to the resin and modeling compound trays and to have a stronger adhesive force to the metallic tray compared with the adhesive agents of Examples 1 to 3.

Examples 5 and 6

Adhesive agents of Examples 5 and 6 having the compositions shown in Table 1 were prepared using polyallyamine (molecular weight: 1,000) as a polyamine compound having 18 amino groups in a molecule.

Examples 7 to 10

Adhesive agents of Examples 7 to 10 having the compositions shown in Table 1 were prepared using polyallyamine (molecular weight: 3,000) as a polyamine compound having 53 amino groups in a molecule.

Examples 11 to 14

Adhesive agents of Examples 11 to 14 having the compositions shown in Table 1 were prepared using polyallyamine (molecular weight: 15,000) as a polyamine compound having 263 amino groups in a molecule.

Example 15

An adhesive agent of Example 15 having the composition shown in Table 1 was prepared using polylysine (molecular weight: 3,500) as a polyamine compound having 25 to 30 amino groups in a molecule.

The adhesive forces of the adhesive agents of Examples 5 to 15 were improved without depending heavily on the types or molecular weights of the polyamine compounds, or the types of the solvents. In particular, those adhesive agents were found to have excellent adhesive forces to the metallic tray. In addition, the adhesive agents containing the polyamine compound in an amount of 30 parts by mass (Examples 6 and 10) were found to have higher adhesive forces to the modeling compound tray. On the other hand, the adhesive agent containing polyallylamine in an amount of 5 parts by mass (Example 7) was found to have a relatively weak adhesive force compared with the adhesive agents containing polyamine compounds in amounts of 10 parts by mass or more.

Next, an adhesion test was performed for adhesive agents each containing an aryl borate compound. Table 2 shows the evaluation results of examples, while Table 3 shows the evaluation results of comparative examples and referential examples. The evaluation method and adhesion test method are the same as the adhesion test for the adhesive agents each containing only a polyamine compound and a solvent, and their descriptions are omitted. The types of trays used, and abbreviations of compounds used in examples, referential examples, and comparative examples are shown in the items (4) and (5), respectively.

(4) Type of Tray
X: A nickel-plated brass tray "COE107" (manufactured by GC Corporation) was used as a metallic tray.
Y1: A tray obtained by forming "OSTRON II" (manufactured by GC Corporation) into a plate by curing was used as a resin tray. A tray obtained by placing a mixture of a powder and liquid of "OSTRON II" on a PP film, further placing another PP film thereon, and curing the resultant product by pressure welding (having a surface roughness (Ra) of 0.1 μm, measured by a contact surface roughness meter (SURFCOM, manufactured by TOKYO SEIMITSU CO., LTD.)) was used.
Y2: A tray obtained by grinding the surface of Y1 with a P600 waterproof abrasive paper while pouring water thereover to make a rough surface (having a surface roughness (Ra) of 1.9 μm, measured by a contact surface roughness meter (SURFCOM, manufactured by TOKYO SEIMITSU CO., LTD.)) was used.
Z: "Modeling Compound (neutral)" (manufactured by GC Corporation) was used as a modeling compound tray.

(5) Abbreviations of Compounds Used in Examples and Comparative Examples
Polyamine Compounds
PA1: 1,7-heptanediamine
PA2: 3,3'-diaminobenzidine
PA3: chitosan (the number of amino groups in a molecule: 6, molecular weight: 984)
PA4: polyallylamine (the number of amino groups in a molecule: 16, molecular weight: 1,000)
PA5: polyallylamine (the number of amino groups in a molecule: 53, molecular weight: 3,000)
PA6: polyallylamine (the number of amino groups in a molecule: 263, molecular weight: 15,000)
Aryl Borate Compounds
AB1: sodium tetraphenylborate
AB2: triethanolammonium tetraphenylborate
AB3: sodium tetrakis(p-fluorophenyl)borate
AB4: sodium butyltri(p-fluorophenyl)borate
AB5: sodium dibutyldiphenylborate
Nitrogen-Containing Compounds
N1: n-butylamine
N2: triethylamine
N3: poly(4-vinylpyridine)
Boron-Containing Compound
B1: tributylborane (Super-Bond catalyst, manufactured by Sunmedical Co. Ltd.)
Another Compound
SPO: stearyl peroxide Example 16

1.5 g of 1,7-heptanediamine (which is a polyamine compound having two amino groups in a molecule), 1.0 g of sodium tetraphenylborate (which is an aryl borate compound), and 7.5 g of ethanol were mixed with stirring to prepare an adhesive agent as a homogenous solution. An adhesion test was performed for the adhesive agent, and as a result, the adhesive agent was found to have relatively good adhesive force to all the trays.

Examples 17 and 18

Adhesive agents having the compositions shown in Table 2 were prepared in the same way as in Example 16 using 3,3'-diaminobenzidine having four amino groups in a molecule and chitosan having six amino groups in a molecule (molecular weight: 984) as polyamine compounds. An adhesion test was performed for the adhesive agent, and as a result, the adhesive agents were found to have excellent adhesive forces to all the trays compared with the adhesive agent of Example 16.

Examples 19 to 33

Adhesive agents having the compositions shown in Table 2 were prepared using, as polyamine compounds, polyallylamine having 18 amino groups in a molecule (molecular weight: 1,000), polyallylamine having 53 amino groups in a molecule (molecular weight: 3,000), and polyallylamine having 263 amino groups in a molecule (molecular weight: 15,000), and using, as aryl borate compounds, sodium tetraphenylborate, triethanolammonium tetraphenylborate, sodium tetrakis(p-fluorophenyl)borate, sodium butyltri(p-fluorophenyl)borate, and sodium dibutyldiphenyl borate. Table 2 shows the results of the adhesion test. The adhesive agents were found to adhere to all the trays firmly or relatively firmly.

TABLE 2

| | Polyamine compound | | | | | | Aryl borate compound | | | | | Solvent | | | Adhesiveness to tray | | | |
|---|---|---|---|---|---|---|---|---|---|---|---|---|---|---|---|---|---|---|
| | PA1 | PA2 | PA3 | PA4 | PA5 | PA6 | AB1 | AB2 | AB3 | AB4 | AB5 | Ethanol | Acetone | Ethyl acetate | X | Y1 | Y2 | Z |
| Example 16 | 15 | — | — | — | — | — | 10 | — | — | — | — | 75 | — | — | △ | △ | ○ | △ |
| Example 17 | — | 15 | — | — | — | — | 10 | — | — | — | — | 75 | — | — | ○ | ○ | ○ | ○ |
| Example 18 | — | — | 15 | — | — | — | 10 | — | — | — | — | 75 | — | — | ○ | ○ | ○ | ○ |
| Example 19 | — | — | — | 15 | — | — | 10 | — | — | — | — | 75 | — | — | ◎ | ◎ | ◎ | ◎ |
| Example 20 | — | — | — | — | 3 | — | 10 | — | — | — | — | 87 | — | — | ○ | ○ | ○ | ○ |
| Example 21 | — | — | — | — | 15 | — | 10 | — | — | — | — | 75 | — | — | ◎ | ◎ | ◎ | ◎ |
| Example 22 | — | — | — | — | 30 | — | 10 | — | — | — | — | 60 | — | — | ◎ | ◎ | ◎ | ◎ |
| Example 23 | — | — | — | — | — | 15 | 10 | — | — | — | — | 75 | — | — | ◎ | ◎ | ◎ | ◎ |
| Example 24 | — | — | — | — | 15 | — | — | 0.5 | — | — | — | 84.5 | — | — | ◎ | △ | ○ | ○ |
| Example 25 | — | — | — | — | 15 | — | — | 3 | — | — | — | 82 | — | — | ◎ | ◎ | ◎ | ◎ |
| Example 26 | — | — | — | — | 15 | — | — | 10 | — | — | — | 75 | — | — | ◎ | ◎ | ◎ | ◎ |
| Example 27 | — | — | — | — | 15 | — | — | 20 | — | — | — | 65 | — | — | ◎ | ◎ | ◎ | ◎ |
| Example 28 | — | — | — | — | 15 | — | — | — | 10 | — | — | 75 | — | — | ◎ | ◎ | ◎ | ◎ |
| Example 29 | — | — | — | — | 15 | — | — | — | — | 10 | — | 75 | — | — | ◎ | ◎ | ◎ | ◎ |
| Example 30 | — | — | — | — | 15 | — | — | — | — | — | 10 | 75 | — | — | ◎ | ○ | ○ | ○ |
| Example 31 | — | — | — | 15 | — | — | 10 | — | — | — | — | — | 75 | — | ◎ | ◎ | ◎ | ◎ |
| Example 32 | — | — | — | 15 | — | — | 10 | — | — | — | — | — | — | 75 | ◎ | ◎ | ◎ | ◎ |
| Example 33 | — | — | — | 10 | 10 | — | 5 | — | — | — | — | 50 | — | 25 | ◎ | ◎ | ◎ | ◎ |

Comparative Examples 1 to 4

A sample including an aryl borate compound and a solvent (Comparative Example 1) was prepared as a system containing no polyamine compound. In addition, samples having the compositions shown in Table 3 were prepared using n-butylamine (which has only one amino group in a molecule) (Comparative Example 2), triethylamine (which is a tertiary amine) (Comparative Example 3), and poly(4-vinylpyridine) (which is a heterocyclic amine compound) (Comparative Example 4). An adhesion test was performed, and it was found that the impression material easily peeled off from all of the trays.

Referential Examples 1 to 3

An adhesion test was performed for a sample prepared in the same way as in Example 16 except that no aryl borate compound was used (Referential Example 1), a sample prepared in the same way as in Example 16 except that a borate compound having no aryl group was used instead of the aryl borate compound (Referential Example 2), and a sample prepared in the same way as in Example 16 except that an organic peroxide was used instead of the aryl borate compound (Referential Example 3). As a result, all the samples were found to have excellent adhesiveness to the metallic tray because the samples contain the polyamine compounds but to have insufficient adhesiveness to the resin tray, in particular, the tray having a surface with small roughness.

TABLE 3

| | Polyamine compound | Nitrogen-containing compound | | | Aryl borate compound | Boron-containing compound | Others | Solvent | Adhesiveness to tray | | | |
|---|---|---|---|---|---|---|---|---|---|---|---|---|
| | PA5 | N1 | N2 | N3 | AB1 | B1 | SPO | Ethanol | X | Y1 | Y2 | Z |
| Comparative Example 1 | — | — | — | — | 10 | — | — | 90 | X | X | X | X |
| Comparative Example 2 | — | 15 | — | — | 10 | — | — | 75 | X | X | X | X |
| Comparative Example 3 | — | — | 15 | — | 10 | — | — | 75 | X | X | X | X |
| Comparative Example 4 | — | — | — | 15 | 10 | — | — | 75 | X | X | X | X |
| Referential Example 1 | 15 | — | — | — | — | — | — | 85 | ◎ | X | △ | △ |
| Referential Example 2 | 15 | — | — | — | — | 10 | — | 75 | ◎ | X | △ | △ |
| Referential Example 3 | 15 | — | — | — | — | — | 5 | 80 | ◎ | X | ◎ | ◎ |

Next, an adhesion test was performed for adhesive agents each containing an organic peroxide. The adhesion test method and conditions thereof are the same as those in the adhesion test for the adhesive agents containing no organic peroxide and aryl borate compound, and their descriptions are omitted.

Tables 4, 5, and 6 show the compositions of the adhesive agents of examples and comparative examples, and the adhesion properties of the adhesive agents. Note that, the initial adhesion properties of the adhesive agents is first described, and then the adhesiveness of the adhesive agents after long-term preservation is described.

TABLE 4

| | Polyamine compound (molecular weight)/parts by mass | Solvent/parts by mass | Organic peroxide/ parts by mass | Adhesiveness to tray (initial) | | |
|---|---|---|---|---|---|---|
| | | | | X | Y | Z |
| Example 34 | 3,3'-Diaminobenzidine/10 | Acetone/85 | Benzoyl peroxide/5 | △ | △ | △ |
| Example 35 | Chitosan (984)/20 | Ethanol/60 + Distilled water/15 | Benzoyl peroxide/5 | ○ | ○ | ○ |
| Example 36 | Polyallylamine (1,000)/10 | Ethanol/85 | Benzoyl peroxide/5 | ◎ | ◎ | ◎ |
| Example 37 | Polyallylamine (3,000)/20 | Ethanol/79 | Benzoyl peroxide/1 | ◎ | ○ | ○ |
| Example 38 | Polyallylamine (3,000)/20 | Ethanol/77 | Benzoyl peroxide/3 | ◎ | ◎ | ◎ |
| Example 39 | Polyallylamine (3,000)/20 | Ethanol/75 | Benzoyl peroxide/5 | ◎ | ◎ | ◎ |
| Example 40 | Polyallylamine (3,000)/10 | Ethanol/80 | Benzoyl peroxide/10 | ◎ | ◎ | ◎ |
| Example 41 | Polyallylamine (3,000)/10 | Ethanol/70 | Benzoyl peroxide/20 | ◎ | ○ | ◎ |
| Example 42 | Polyallylamine (3,000)/10 | Ethanol/85 | Benzoyl peroxide/5 | ◎ | ◎ | ◎ |
| Example 43 | Polyallylamine (3,000)/20 | Isopropyl alcohol/75 | Benzoyl peroxide/5 | ◎ | ◎ | ◎ |
| Example 44 | Polyallylamine (3,000)/20 | Acetone/75 | Benzoyl peroxide/5 | ◎ | ◎ | ◎ |
| Example 45 | Polyallylamine (3,000)/20 | Ethanol/50 + Acetone/25 | Benzoyl peroxide/5 | ◎ | ◎ | ◎ |
| Example 46 | Polyallylamine (3,000)/20 | Ethanol/70 + Distilled water/5 | Benzoyl peroxide/5 | ◎ | ◎ | ◎ |
| Example 47 | Polyallylamine (3,000)/20 | Ethanol/70 + Distilled water/5 | Stearoyl peroxide/5 | ◎ | ◎ | ◎ |
| Example 48 | Polyallylamine (3,000)/20 | Ethanol/75 | 1,1-Bis(t-butylperoxy) 3,3,5-trimethylcyclohexane/5 | ◎ | ○ | ○ |
| Example 49 | Polyallylamine (3,000)/15 + Polyallylamine (15,000)/5 | Ethanol/70 + Distilled water/5 | Benzoyl peroxide/5 | ◎ | ◎ | ◎ |
| Example 50 | Polyallylamine (15,000)/15 | Ethanol/80 | Benzoyl peroxide/5 | ◎ | ◎ | ◎ |
| Example 51 | Polyallylamine (15,000)/15 | Isopropyl alcohol/80 | Benzoyl peroxide/5 | ◎ | ◎ | ◎ |
| Example 52 | Polylysine (3,500)/20 (15,000)/15 | Ethanol/35 + Distilled water/40 | Benzoyl peroxide/5 | ◎ | ◎ | ◎ |

Example 34

An adhesive agent having the composition shown in Table 4 was prepared using benzoyl peroxide as an organic peroxide and 3,3'-diaminobenzidine as a polyamine compound. The adhesive agent of Example 34 was found to have a higher adhesive force particularly to each of the resin and modeling compound trays compared with the adhesive agent containing no organic peroxide (Example 3).

Example 35

An adhesive agent having the composition shown in Table 4 was prepared using benzoyl peroxide as an organic peroxide and chitosan (molecular weight: 984) as a polyamine compound. The adhesive agent of Example 35 was found to have a higher adhesive force particularly to each of the resin and modeling compound trays compared with the adhesive agent containing no organic peroxide (Example 4). Meanwhile, the adhesive agent containing chitosan (Example 35) was found to have a higher adhesive force compared with the adhesive agent containing 3,3'-diaminobenzidine (Example 34).

Example 36

An adhesive agent having the composition shown in Table 4 was prepared using benzoyl peroxide as an organic peroxide and polyallylamine (molecular weight: 1,000) as a polyamine compound. The adhesive agent of the Example 36 was found to have a high adhesive force to all the trays.

Examples 37 to 41

Adhesive agents were prepared, each using benzoyl peroxide as an organic peroxide and polyallylamine (molecular weight: 3,000) as a polyamine compound so that the adhesive agents have different content and the like of benzoyl peroxide as shown in Table 4.

Examples 42 to 46

Adhesive agents were prepared, each using benzoyl peroxide as an organic peroxide and using polyallylamine (molecular weight: 3,000) as a polyamine compound so that the adhesive agents have different mass ratios of polyallylamine, solvents, and mass ratios thereof as shown in Table 4.

Examples 47 and 48

Adhesive agents having the compositions shown in Table 4 were prepared, each using stearoyl peroxide and 1,1-bis(t-butylperoxy)3,3,5-trimethylcyclohexane as organic peroxides and using polyallylamine (molecular weight: 3,000) as a polyamine compound. When comparing the adhesive agent of Example 46 or 47 containing a diacyl peroxide (benzoyl peroxide or stearoyl peroxide) and the adhesive agent of Example 48 containing a peroxyketal (1,1-bis(t-butylperoxy) 3,3,5-trimethylcyclohexane), the adhesive agent of Example 46 or 47 was found to have a higher adhesive force particularly to each of the resin and modeling compound trays than that of the adhesive agent of Example 48.

Example 49

An adhesive agent having the composition shown in Table 4 was prepared using benzoyl peroxide as an organic peroxide and polyallylamine (molecular weight: 3,000) and polyallylamine (molecular weight: 15,000) as a polyamine compound.

Examples 50 and 51

Adhesive agents having the composition shown in Table 4 were prepared, each using benzoyl peroxide as an organic peroxide and polyallylamine (molecular weight: 15,000) as a polyamine compound.

Example 52

An adhesive agent having the composition shown in Table 4 was prepared using benzoyl peroxide as an organic peroxide and polylysine (molecular weight: 3,500) as a polyamine compound.

The adhesive agents containing benzoyl peroxide in an amount ranging from 3 parts by mass or more to 10 parts by mass or less and the polyamine compound in an amount of 10 parts by mass or more were found to have very high adhesive forces to all the trays. The adhesive agents each containing benzoyl peroxide in an amount of 1 part by mass and 20 parts by mass (Examples 37 and 41) were found to have higher adhesive forces to the resin tray and modeling compound tray compared to those of the adhesive agents containing no benzoyl peroxide (Examples 8 and 9). However, the adhesive agents of Examples 37 and 41 were found to have lower adhesive forces than those of the adhesive agents containing benzoyl peroxide in an amount ranging from 3 parts by mass or more to 10 parts by mass or less and the polyamine compound in an amount of 10 parts by mass or more.

group in a molecule), triethylamine (which is a tertiary amine), poly(4-vinylpyridine) (which is a heterocyclic amine compound), and quaternary poly(2-methacryloyloxyethyl phosphorylcholine). When the impression materials were removed from all the trays where the samples of Comparative Examples 7 to 12 were applied, the impression materials easily peeled off from the trays.

Test Method of Adhesive Ability after Long-Term Preservation

The materials shown in Table 6 were mixed to prepare various adhesive agents. After preparation, the adhesive agents were sealed and preserved in an incubator at 37° C. for 9 weeks. The adhesive abilities of the adhesive agents after

TABLE 5

|  | Nitrogen-containing compound/parts by mass | Type of solvent/ parts by mass | Peroxide/ parts by mass | Adhesiveness to tray (initial) | | |
|---|---|---|---|---|---|---|
|  |  |  |  | X | Y | Z |
| Comparative Example 5 | — | Ethanol/100 | — | X | X | X |
| Comparative Example 6 | — | Ethanol/95 | Benzoyl peroxide/5 | X | X | X |
| Comparative Example 7 | n-Butylamine/15 | Ethanol/85 | — | X | X | X |
| Comparative Example 8 | n-Butylamine/30 | Ethanol/60 + Distilled water/10 | — | X | X | X |
| Comparative Example 9 | Triethylamine/15 | Ethanol/85 | — | X | X | X |
| Comparative Example 10 | Poly(4-vinylpyridine)/15 | Ethanol/85 | — | X | X | X |
| Comparative Example 11 | Poly(2-methacryloyloxyethyl | Ethanol/10 + Distilled water/60 | — | X | X | X |
| Comparative Example 12 | Poly(2-methacryloyloxyethyl | Ethanol/85 | — | X | X | X |

Comparative Examples 5 to 12

A sample containing only ethanol (Comparative Example 5), and a sample obtained by adding the organic peroxide to ethanol according to the composition shown in Table 5 (Comparative Example 6) were prepared as a system containing no polyamine compound. The trays where the samples of Comparative Examples 5 and 6 were applied did not adhere to the impression material. According to the compositions shown in Table 5, samples of Comparative Examples 7 to 12 were prepared using n-butylamine (which has only one amino long-term preservation were evaluated in the same way as in the above-mentioned test on the initial adhesive abilities. The alginate impression material, tray, and reference of evaluation are the same as those in the case of the above-mentioned test method of the initial adhesive abilities of the adhesive agents containing no organic peroxide and no aryl borate compound.

Abbreviated name of used α-alkyl styrene dimer

DMP: 2,4-diphenyl-4-methyl-1-pentene

DMH: 2,4-diphenyl-4-methyl-1-hexene

DEH: 2,4-diphenyl-4-ethyl-1-hexene

TABLE 6

|  | Polyamine compound (molecular weight)/ parts by mass | Solvent/ parts by mass | Organic peroxide/ parts by mass | α-Alkylstyrene dimer/ parts by mass | Adhesiveness to tray (initial) | | | Adhesiveness to tray (after preservation) | | |
|---|---|---|---|---|---|---|---|---|---|---|
|  |  |  |  |  | X | Y | Z | X | Y | Z |
| Example 53 | Polyallylamine (3,000)/20 | Ethanol/74.9 | Benzoyl peroxide/5 | DMP/0.1 | ◎ | ◎ | ◎ | ◎ | ◎ | ◎ |
| Example 54 | Polyallylamine (3,000)/20 | Ethanol/74.5 | Benzoyl peroxide/5 | DMP/0.5 | ◎ | ◎ | ◎ | ◎ | ◎ | ◎ |
| Example 55 | Polyallylamine (3,000)/20 | Ethanol/74 | Benzoyl peroxide/5 | DMP/1 | ◎ | ◎ | ◎ | ◎ | ◎ | ◎ |
| Example 56 | Polyallylamine (3,000)/20 | Ethanol/72 | Benzoyl peroxide/5 | DMP/3 | ◎ | ◎ | ◎ | ◎ | ◎ | ◎ |
| Example 57 | Polyallylamine (3,000)/20 | Ethanol/70 | Benzoyl peroxide/5 | DMP/5 | ○ | ○ | ○ | ○ | ○ | ○ |
| Example 58 | Polyallylamine (3,000)/20 | Ethanol/74.5 | Benzoyl peroxide/5 | DMH/0.5 | ◎ | ◎ | ◎ | ◎ | ◎ | ◎ |
| Example 59 | Polyallylamine (3,000)/20 | Ethanol/74.5 | Benzoyl peroxide/5 | DEH/0.5 | ◎ | ◎ | ◎ | ◎ | ◎ | ◎ |
| Example 60 | Polyallylamine (3,000)/10 | Ethanol/69.5 | Benzoyl peroxide/20 | DMP/0.5 | ◎ | ○ | ◎ | ◎ | ○ | ◎ |

TABLE 6-continued

| | Polyamine compound (molecular weight)/ parts by mass | Solvent/ parts by mass | Organic peroxide/ parts by mass | α-Alkylstyrene dimer/ parts by mass | Adhesiveness to tray (initial) | | | Adhesiveness to tray (after preservation) | | |
|---|---|---|---|---|---|---|---|---|---|---|
| | | | | | X | Y | Z | X | Y | Z |
| Example 61 | Chitosan (984)/20 | Ethanol/59.5 + Distilled water/15 | Benzoyl peroxide/5 | DMP/0.5 | ○ | ○ | ○ | ○ | ○ | ○ |
| Example 62 | Polyallylamine (3,000)/20 | Ethanol/69.5 + Distilled water/5 | Stearoyl peroxide/5 | DMP/0.5 | ◎ | ◎ | ◎ | ◎ | ◎ | ◎ |
| Referential Example 4 (Example 39) | Polyallylamine (3,000)/20 | Ethanol/75 | Benzoyl peroxide/5 | — | ◎ | ◎ | ◎ | ◎ | Δ | Δ |
| Referential Example 5 (Example 41) | Polyallylamine (3,000)/10 | Ethanol/70 | Benzoyl peroxide/20 | — | ◎ | ○ | ◎ | ◎ | Δ | Δ |
| Referential Example 6 (Example 35) | Chitosan (984)/20 | Ethanol/60 + Distilled water/15 | Benzoyl peroxide/5 | — | ○ | ○ | ○ | ○ | Δ | Δ |
| Referential Example 7 (Example 47) | Polyallylamine (3,000)/20 | Ethanol/70 + Distilled water/5 | Stearoyl peroxide/5 | — | ◎ | ◎ | ◎ | ◎ | Δ | Δ |
| Referential Example 8 (Example 9) | Polyallylamine (3,000)/20 | Ethanol/80 | — | — | ◎ | Δ | Δ | ◎ | Δ | Δ |

Examples 53 to 62

Adhesive agents of Examples 53 to 57 containing DMP as an α-alkylstyrene dimer were prepared so that the adhesive agents have different concentrations of DMP. Meanwhile, adhesive agents of Examples 58 and 59 were prepared using other α-alkylstyrene dimers. In addition, an adhesive agent of Example 60 containing benzoyl peroxide as a peroxide was prepared so that the adhesive agent has a different concentrations of benzoyl peroxide. Further, an adhesive agent of Example 61 containing a different polyamine compound and an adhesive agent of Example 62 containing a different organic peroxide were prepared. The adhesive agents of Examples 53 to 62 containing the α-alkylstyrene dimer were found to have very high adhesive forces to all the trays even after preservation at 37° C. for 9 weeks. As compared with corresponding Referential Examples 4 to 8 (adhesive agents containing a peroxide: Examples 39, 41, 35, and 47) and Referential Example 8 (adhesive agent containing no peroxide: Example 9), the adhesive agents were found to have high adhesive forces to the resin tray and modeling compound tray even after long-term preservation.

INDUSTRIAL APPLICABILITY

The present invention can be used in the field of dental treatment in which a mold of teeth is produced using an alginate impression material.

The invention claimed is:

1. An adhesive agent for adhesion between an alginate impression material and an impression tray for dental applications comprising
   (A) a polyamine compound having two or more —NH$_2$ groups in a molecule;
   (B) a solvent;
   (C) an organic peroxide, and
   (E) a compound represented by the following general formula (2):

[Chem 2]

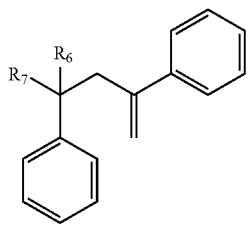

(2)

where $R^6$ and $R^7$ each independently represent a hydrogen atom or an alkyl group with 1 to 3 carbon atoms.

2. A kit, comprising:
   an adhesive agent for adhesion between an alginate impression material and an impression tray for dental applications, the adhesive agent comprising:
   (A) a polyamine compound having two or more —NH$_2$ groups in a molecule;
   (B) a solvent;
   (C) an organic peroxide; and a paste alginate impression material.

3. The kit according to claim 2, wherein the adhesive agent further comprises (E) a compound represented by the following general formula (2):

[Chem 2]

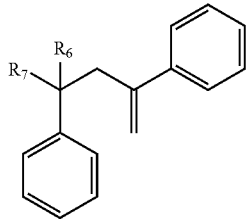

(2)

where $R^6$ and $R^7$ each independently represent a hydrogen atom or an alkyl group with 1 to 3 carbon atoms.

4. The kit according to claim 2, wherein the solvent is at least one selected from alcohols, acetone, and acetate ester.

5. The kit according claim 2, wherein the polyamine compound is a polyamine compound having 5 or more —$NH_2$ groups in a molecule.

* * * * *